United States Patent
Slotman

Patent Number: 5,690,606
Date of Patent: Nov. 25, 1997

[54] TISSSUE SPREADING SURGICAL INSTRUMENT

[76] Inventor: Gus J. Slotman, 705 Mill St., Moorestown, N.J. 08057

[21] Appl. No.: 608,043

[22] Filed: Feb. 28, 1996

Related U.S. Application Data

[63] Continuation of Ser. No. 262,625, Jun. 20, 1994, abandoned.

[51] Int. Cl.$^6$ ..................................................... A61B 11/02
[52] U.S. Cl. ........................... 600/206; 600/201; 600/204; 600/210; 600/219; 606/205
[58] Field of Search ........................... 600/201, 204, 600/206, 210, 219; 606/205, 206, 207, 208

[56] References Cited

U.S. PATENT DOCUMENTS

| | | | |
|---|---|---|---|
| 4,190,042 | 2/1980 | Sinnreich | 128/20 |
| 4,909,789 | 3/1990 | Taguchi et al. | 604/107 |
| 5,152,279 | 10/1992 | Wilk | 128/17 |
| 5,176,128 | 1/1993 | Andrese | 600/206 X |
| 5,178,133 | 1/1993 | Pena | 128/20 |
| 5,195,505 | 3/1993 | Josefsen | 128/20 |
| 5,195,506 | 3/1993 | Hulfish | 128/20 |
| 5,199,419 | 4/1993 | Remiszewski et al. | 128/20 |
| 5,224,954 | 7/1993 | Watts et al. | 606/205 |
| 5,235,966 | 8/1993 | Jamner | 128/20 |
| 5,271,385 | 12/1993 | Bailey | 128/20 |
| 5,275,610 | 1/1994 | Eberbach | 606/198 |
| 5,280,782 | 1/1994 | Wilk | 128/20 |
| 5,304,183 | 4/1994 | Gourlay et al. | 606/205 X |
| 5,308,357 | 5/1994 | Lichtman | 606/205 |
| 5,325,848 | 7/1994 | Adams et al. | 600/206 |
| 5,330,502 | 7/1994 | Hassler et al. | 606/205 |
| 5,345,927 | 9/1994 | Bonutti | 600/204 X |
| 5,352,237 | 10/1994 | Rodak et al. | 128/20 X |
| 5,376,094 | 12/1994 | Kline | 606/205 X |

FOREIGN PATENT DOCUMENTS

| | | | |
|---|---|---|---|
| 3717657 | 12/1988 | Germany | 600/204 |
| 9418893 | 9/1994 | WIPO | 606/205 |

Primary Examiner—Beverly M. Flanagan
Attorney, Agent, or Firm—Law Offices of Jane Massey Licata

[57] ABSTRACT

A tissue spreading surgical instrument having a handle assembly which includes a moveable handle assembly; an elongated shaft extending distally from said handle assembly which houses an actuating mechanism moveable in response to movement of the handle assembly and a tissue spreading assembly comprising a plurality of fingers operatively associated with the distal end of the shaft and deployable between a closed and open position wherein the fingers are spread in opposite direction by the actuation mechanism in response to movement of the handle assembly is provided.

18 Claims, 2 Drawing Sheets

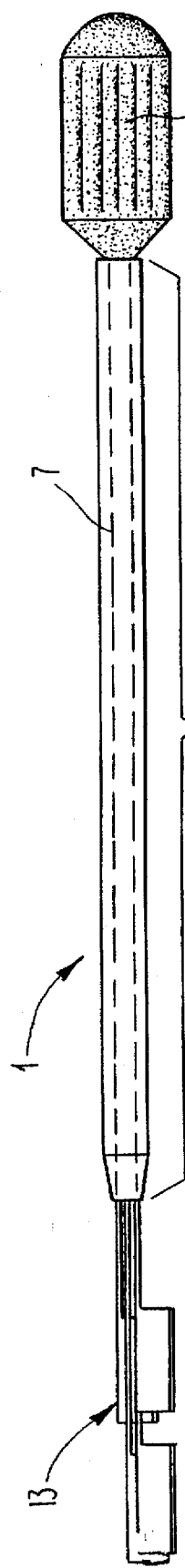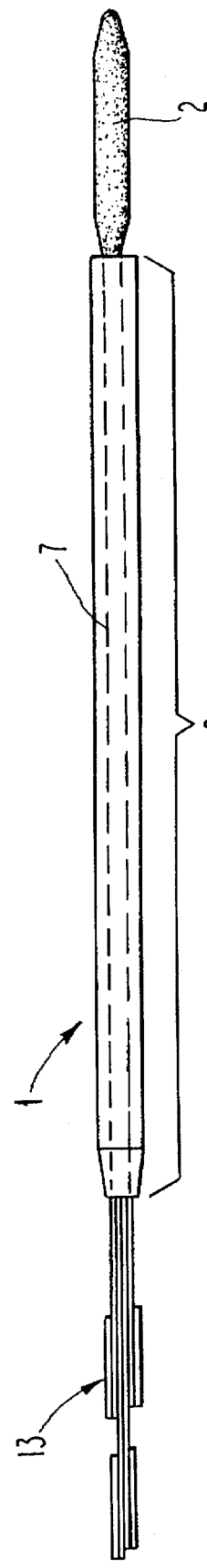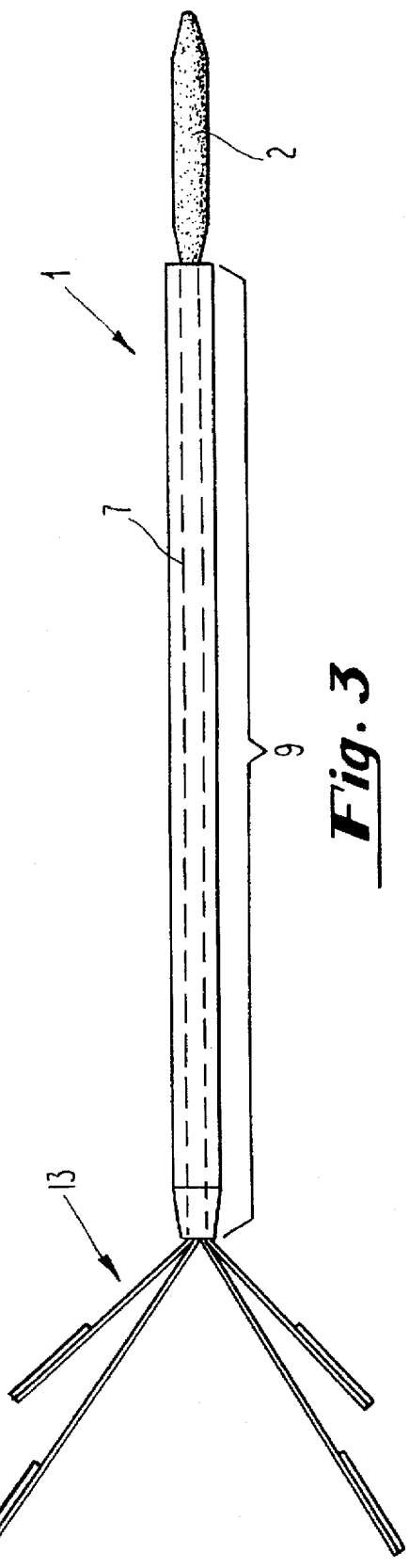

TISSSUE SPREADING SURGICAL INSTRUMENT

This is a continuation of application Ser. No. 08/262,625, filed Jun. 20, 1994, now abandoned.

FIELD OF THE INVENTION

The invention relates to a tissue spreading surgical instrument and, more particularly, to an endoscopic tissue spreading surgical instrument. The instrument is especially useful in endoscopic discectomy procedures and other minimally invasive spinal procedures.

BACKGROUND OF THE INVENTION

In endoscopic or laparoscopic procedures, one or more small incisions are made in the surrounding body walls, generally by use of a trocar having an obturator with a sharp tip removably positioned in a cannula. After penetration, the obturator is removed leaving the cannula positioned in the abdominal cavity for reception of a camera or endoscope to transmit images to a remote TV monitor. Specialized instruments for performing and facilitating observations and/or surgical procedures are inserted through other trocar sites while being viewed by the physician on the monitor. Procedures performed endoscopically have been shown to be advantageous in significantly reducing the costs of a surgical procedure by shortening the patient's hospital stay and recovery period so that the patient can resume normal activities much sooner. A number of instruments useful in endoscopic observational and surgical procedures have been described.

During endoscopic surgery, as in most types of surgery, there is a need to move tissue in the operating field. In general, a retractor is an instrument for drawing aside the edges of a wound or for holding back structures adjacent to the operative field. A number of retractors and forceps have been described in the art which operate very similarly to open surgery retractors but which can be used in endoscopic surgical procedures. Examples of these endoscopic retractors are described in U.S. Pat. No. 5,280,782, U.S. Pat. No. 5,275,610, U.S. Pat. No. 5,235,966, U.S. Pat. No. 5,271,385, U.S. Pat. No. 5,199,419, U.S. Pat. No. 5,195,506, U.S. Pat. No. 5,195,505, U.S. Pat. No. 5,178,133, U.S. Pat. No. 5,152,279, and U.S. Pat. No. 4,909,789. In general, these instruments comprise a straight shaft member with one end having a plurality of linear members or blades which have a closed position and an open position. The shaft member is inserted through an incision or trocar into the body cavity with the linear members in the closed position. The linear members are then moved to the open position and the obstructing organ or tissue is moved aside by these members by the surgeon placing pressure upon the shaft of the instrument and bracing the instrument shaft against the wall of the body cavity which is used as a fulcrum. A variety of different mechanisms are disclosed for deploying the linear members from a closed to an open position for these retractors. These instruments are satisfactory in endoscopic procedures wherein the obstructive tissues or organ can be moved unidirectionally out of the field and can tolerate some tissue pressure. However, these retractors do not retract in two opposite directions at the same time and therefore do not provide the control necessary for surgeons to perform delicate surgeries such as lumbar discectomies wherein the surrounding tissues which may be obstructive include fragile nerves, arteries, veins or hollow organs such as the ureters. These instruments also place additional unwanted pressure against the body cavity wall during manipulation and movement of the obstructing tissue. Therefore, there still remains a need for endoscopic instrumentation which properly and atraumatically improve visibility and accessibility within the body cavity.

SUMMARY OF THE INVENTION

An object of the present invention is to provide a tissue spreading surgical instrument primarily used in endoscopic surgery which is capable of spreading the tissues in opposite directions and allows for control of the amount of extension of the tissue spreading means and/or angular position of the tissue spreading means by the surgeon so that the surgeon may accurately position and control the tissue spreading means to facilitate the surgical procedure and minimize trauma to surrounding tissues.

BRIEF DESCRIPTION OF DRAWINGS

FIG. 1 is a side view of an instrument for spreading soft tissue illustrating the tissue spreading assembly in a generally closed position.

FIG. 2 is a top view of the instrument provided in FIG. 1.

FIG. 3 is a top view of the instrument illustrating the fingers of the tissue spreading assembly in a generally open position.

DETAILED DESCRIPTION OF THE INVENTION

Figure 4:
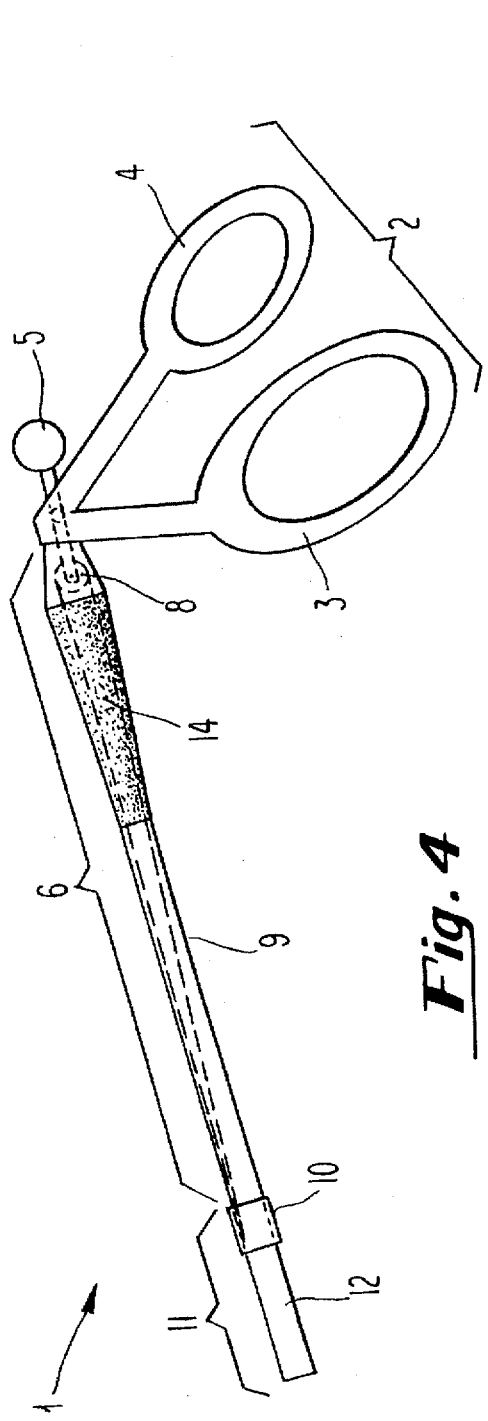
FIG. 4 is a side view of a preferred embodiment of an instrument for spreading soft tissue illustrating the tissue spreading assembly in the closed position condition.

Referring now in specific detail to the drawings, in which like reference numbers identify similar or identical elements, FIGS. 1–5 illustrate embodiments of a surgical tissue spreading instrument shown generally at 1. In simplest terms, the tissue spreading instruments can be broken down into a handle means 2, a shaft 9 and a plurality of fingers for spreading the tissues 13. The embodiments of FIGS. 1–3 and 4–5 are adapted for and particularly useful in endoscopic or laparoscopic procedures wherein at least an endoscopic portion of the surgical tissue spreader 1 is inserted into the operative site through a cannula or open wound (not shown).

In one embodiment, as shown in FIGS. 1–3, the handle assembly 2 of the surgical tissue spreader 1 comprises a screwing mechanism. The screwing mechanism is inserted into an hollow elongated shaft 9 and operatively associated with an actuation mechanism 7 located in the shaft 9. The actuation mechanism 7 is located in the proximal end of the shaft 9 and extends to the distal end where it is connected to the tissue spreading assembly. In this embodiment, the tissue spreading assembly comprises a plurality of fingers 13 which are capable of moving from a closed position as shown in FIGS. 1 and 2 to an open position as shown in FIG. 3. The fingers of the tissue spreading assembly may either be rigid or flexibly resilient depending upon the surgical procedure for which the instrument is being used. In this embodiment, it is preferred that the fingers be more rigid. The actuation mechanism 7 moves in response to rotation of the screwing mechanism and causes the opening or closing of the fingers 13 of the tissue spreading assembly. The actuation mechanism may comprise any appropriate means for connecting the rotating screw to the tissue spreading assembly and functions to move the fingers of the tissue spreading assembly between open and closed positions. An example of an actuating mechanism for use in this embodiment is a screw shaft and wheel mechanism. In a preferred embodiment, there are four fingers which make up the plurality of fingers, each finger ranging in length from about 3 to about 15 centimeters and width from about 10 to about 12 millimeters. The fingers move in opposing directions so that together they are capable of spreading the tissue from about 2 to about 15 centimeters. This instrument is especially useful in endoscopic procedures as rotation of the screwing mechanism causes the fingers of the tissue spreading assembly to open resulting in the obstructing tissue being spread. No pressure need be placed on the shaft of the instrument or on the body cavity wall as the surgeon spreads the tissues. In endoscopic procedures, it is preferred that the length of the shaft plus the fingers ranges from about 30 to about 32 centimeters.

Figure 5:
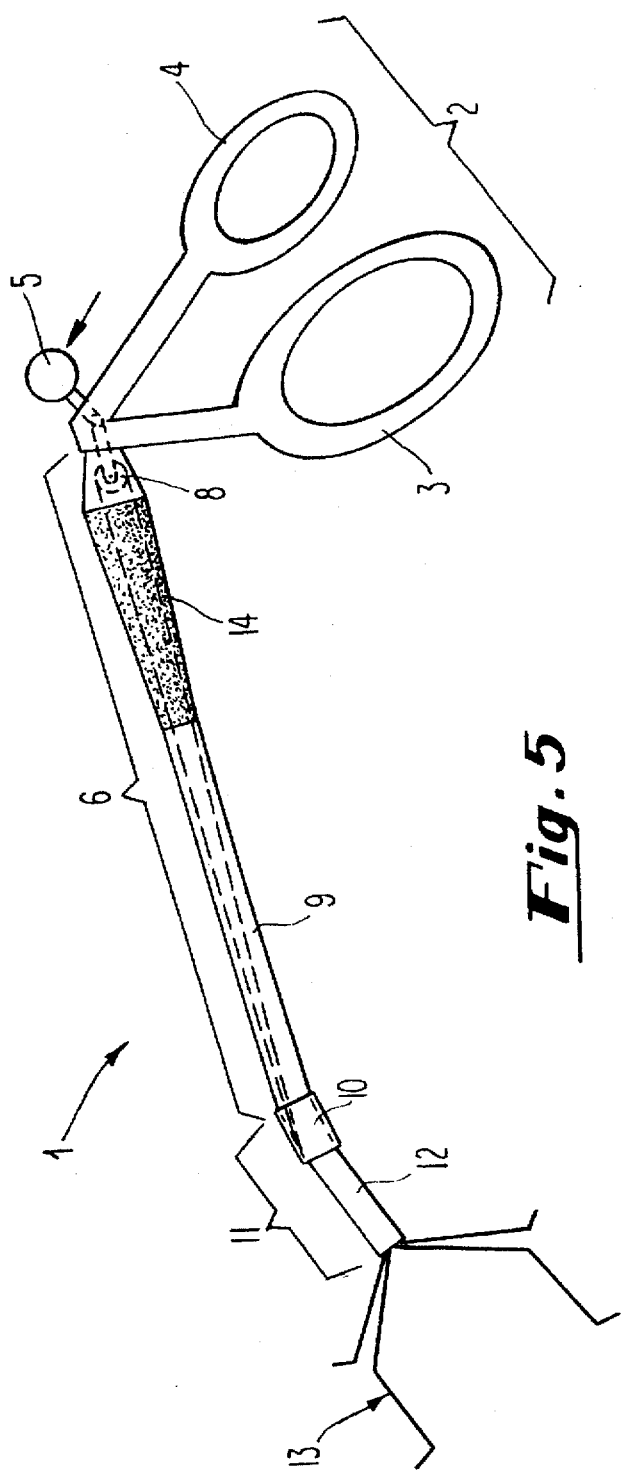
FIG. 5 is a side view of the instrument of FIG. 4 illustrating the tissue spreading members in a generally open position being extended from the housing assembly which is angled in accordance with movement of the roticulation control.

In another embodiment, as shown in FIGS. 4–5, the tissue spreading surgical instrument of the present invention comprises a handle assembly 2 which has a moveable front finger grip 3 and a stationary back finger grip 4. In a preferred embodiment, finger loops are provided at the lower end of the finger grips. However, other means for holding the instrument are contemplated. Examples include, but are not limited to, pistol grips, palm grips, axial grips or ring grips. A shaft member 6 comprising a hollow elongated shaft 9 is attached to and extends distally from the handle assembly 2. While it is preferred that the shaft 9 be circular in the cross section so as to occupy a minimal area, the shaft can be square, rectangular or any other cross section that is desired or convenient. In a preferred embodiment, the shaft 9 is rotatable. There are a variety of means for achieving this rotation, including but not limited to, placing a finger grooved barrel or textured area 14 on the outer surface of the shaft 9 near the proximal end. The length of the shaft 9 will vary depending upon the primary use for the tissue spreading instrument 1. If the primary use for the instrument is in endoscopic procedures, it is preferred that the shaft 9 be from about 15 to about 30 centimeters in length. The shaft 9 serves as a housing means for an actuating mechanism located in the proximal end and extending at least partially through the shaft 9 to the distal end. The actuating mechanism connects the moveable front finger grip 3 of the handle assembly 2 to the tissue spreading assembly 11. In this embodiment, the actuation mechanism may comprise any appropriate means for connecting the front finger grip 3 to the tissue spreading assembly 11 and functions to spread the fingers 13 of the tissue spreading assembly 11 between open and closed positions. Examples of actuating mechanisms which can be used in the present invention include, but are not limited to, a cable and pulley system and a screw shaft and wheel mechanism.

In one embodiment, the tissue spreading assembly 11 is operatively associated with the distal end of the shaft 9 and includes a plurality of fingers 13. The fingers may either be rigid or flexibly resilient depending upon the surgical procedure in which the instrument is used. In this embodiment, it is preferred that the fingers by flexibly resilient. Examples of materials which these flexible resilient fingers can be comprised of include, but are not limited to, surgical steel, plastic, and aluminum. In a closed position, the fingers 3 are withdrawn into the distal end of the shaft 9. Upon movement of the front finger grip 3, however, the actuating mechanism 7 causes the fingers 13 to be extended from the distal end of the shaft 9 transversely with respect to the shaft 9. The width to which the fingers 13 can be transversely deployed is dependent upon the intended use of the surgical instrument. If the intended use is for endoscopic procedures, it is preferred that the fingers 13 be transversely deployable in opposite directions so that the total width spread ranges from about 5 to about 15 centimeters. The amount of extension of the fingers 13 is directly controlled by the movement of the finger grip 3. Each finger 13 can range in size depending upon the intended use of the surgical instrument. If the intended use is for endoscopic procedures, the preferred length for each of the fingers 13 ranges from about 2 to about 10 centimeters in length.

In a preferred embodiment, the tissue spreading instrument 1 further comprises a locking ratchet mechanism operatively associated with the front finger grip 3. This locking ratchet mechanism controls the movement and locks into a selected position the front finger grip 3 so that once the amount of extension and placement of the fingers 13 are chosen, they can also be fixed.

In another embodiment, as depicted in FIGS. 4–5, the handle assembly 2 of the tissue spreading surgical instrument 1 further comprises a roticulation control 5 for manipulation of a roticulating joint 10. It is preferred that the roticulation control 5 comprise a thumb screw or a spring mechanism controlled by thumb pressure so that movement of the control can be performed by simple movement of the user's thumb. In this embodiment, depicted in FIG. 4, the shaft 9 attached to and extending distally from the handle assembly 2 defines a longitudinal axis of the instrument. It is preferred that the shaft 9 be rotatable as described previously. In addition to the actuating mechanism, a roticulating mechanism 8 is housed in the proximal end of the shaft 9 and extends at least partially through the shaft 9 to the distal end. This roticulation mechanism 8 attaches the roticulation control 5 in the handle assembly 2 to a roticulating joint 10 located at the distal end of the shaft 9. Any appropriate means for connecting the roticulation control to the roticulating joint which is capable of moving the joint in response to movement of the roticulation control can serve as a roticulating mechanism. Examples of roticulating mechanisms include, but are not limited to, a cable and pulley system and a screw shaft and wheel mechanism. A housing segment 12 is attached longitudinally to the distal end of the shaft 9 by means of this roticulating joint 10. The roticulating joint 10 is operatively associated with the roticulating mechanism 8 and manipulates the housing segment 12 transversely relative to the longitudinal axis of the instrument in response to movement of the roticulation control 5. In this embodiment, the tissue spreading assembly 11 is housed in the housing segment 12. Upon movement of the front finger grip 3 of the handle assembly 2, the fingers 13 are extended from the housing segment 12 as depicted in FIG. 5. As also depicted in FIG. 5, the angle of the housing segment 12 and fingers 13 with respect to the rest of the surgical instrument can be altered by movement of the roticulation control 5.

In a preferred embodiment, the roticulation control 5 may also further comprise a locking ratchet mechanism, so that once the angle of the housing segment 12 and fingers 13 has been selected, the roticulation control 5 can be locked so that the selection is fixed.

Instruments of the present invention can be used in any surgical procedure to move or spread obstructing tissues. In a preferred embodiment, the instruments of the present invention are used in endoscopic procedures. Surgeons performing an endoscopic surgical procedure can insert the distal end of the shaft with the tissue spreading assembly in the withdrawn position into the body cavity through a cannula or incision in the body wall. By viewing the procedure on the camera, the surgeon can manipulate the instrument to the selected area. In the first embodiment, upon positioning of the instrument, the tissue may be spread by turning of the handle assembly which results in opening of the plurality of fingers. In the second embodiment, once positioned, the fingers of the tissue spreading assembly can be deployed and extended from either the distal end of the shaft or the housing segment by moving the front finger grip. In either embodiment, no pressure is placed on the body cavity wall as the surgeon is not required to place pressure on the shaft to spread the tissue. In a preferred embodiment of the invention, the angle of the fingers of the instrument with respect to the instrument can be altered by moving the roticulation control. Thus, the width to which the obstructing tissue is spread and the angular position to where it is moved are selected and controlled by the surgeon. Once selected, the position of the fingers can be locked by the ratchet locking mechanism on the instrument thus freeing the surgeon's hands for the surgical procedure.

What is claimed is:

1. A tissue spreading surgical instrument comprising:

a handle assembly capable of movement;

an elongated shaft extending distally from said handle assembly, said shaft having a proximal and distal end, said proximal end for housing an actuating mechanism;

an actuating mechanism housed in said proximal end of said shaft and at least partially extending through said shaft to said distal end, said actuating mechanism moveable in response to movement of said handle assembly;

a tissue spreading assembly operatively associated with said distal end of said shaft and deployable between a closed and open position by said actuation mechanism in response to movement of said handle assembly, said tissue spreading assembly including a plurality of fingers, wherein in the closed position said fingers maintain a longitudinal axis with said instrument and in the open position said fingers are spread in opposing directions to one another and transversely with respect to said shaft so that tissues can be spread apart without placing pressure on the elongated shaft of the tissue spreading surgical instrument or on a body cavity wall.

2. The tissue spreading instrument of claim 1 wherein said handle assembly comprises a screwing mechanism.

3. The tissue spreading instrument of claim 1 wherein said elongated shaft together with the fingers range in length from 30 to 32 centimeters.

4. The tissue spreading instrument of claim 3 wherein the instrument is used in endoscopic surgical procedures.

5. The tissue spreading surgical instrument of claim 3 wherein said plurality of fingers are variable in length, each finger ranging from 3 to 15 centimeters in length.

6. The tissue spreading surgical instrument of claim 3 wherein in the open position, said plurality of fingers are transversely deployed to a width ranging from 2 to 15 centimeters.

7. The tissue spreading surgical instrument of claim 1 wherein the fingers are rigid.

8. A tissue spreading surgical instrument comprising:

a handle assembly having a moveable front finger grip and a stationary back finger grip;

a rotatable, elongated shaft extending distally from said handle assembly, said shaft having an inner and outer surface and a proximal and distal end, said proximal end for housing an actuating mechanism;

an actuating mechanism housed in said proximal end of said shaft and at least partially extending through said shaft to said distal end, said actuating mechanism moveable in response to movement of said front finger grip;

a tissue spreading assembly operatively associated with said distal end of said shaft and deployable between a closed and open position by said actuation mechanism in response to movement of said front finger grip, said tissue spreading assembly including a plurality of flexible resilient fingers, wherein in the closed position said flexible resilient fingers are withdrawn into said distal end of said shaft and in the open position said flexible resilient fingers are extended from said distal end of said shaft transversely with respect to said shaft so that tissues can be spread.

9. The tissue spreading surgical instrument of claim 8 further comprising a means for rotating said elongated shaft, said means being located on said outer surface of said proximal end of said rotatable elongated shaft.

10. The tissue spreading surgical instrument of claim 8 wherein said plurality of resilient flexible fingers are variable in length, each resilient flexible finger ranging from 2 to 10 centimeters in length.

11. A tissue spreading surgical instrument comprising:

a handle assembly having a moveable front finger grip, a stationary back finger grip and a roticulation control for manipulation of a roticulating joint;

an elongated shaft extending distally from said handle assembly and defining a longitudinal axis of the instrument, said elongated shaft having an outer and inner surface and a proximal and distal end, said proximal end for housing an actuating mechanism and a roticulating mechanism;

an actuating mechanism housed in said proximal end of said elongated shaft and at least partially extending through said elongated shaft to said distal end, said actuating mechanism moveable in response to movement of said front finger grip;

a roticulating mechanism housed in said proximal end of said elongated shaft and at least partially extending through said elongated shaft to said distal end, said roticulating mechanism moveable in response to movement of said roticulation control;

a housing segment attached longitudinally to said distal end of said elongated shaft by means of a roticulating joint;

said roticulating joint operatively associated with said roticulating mechanism for manipulating said housing segment transversely relative to the longitudinal axis of the instrument in response to movement of said roticulation control; and a tissue spreading assembly operatively associated with said housing segment and deployable between a closed and open position by said actuation mechanism in response to movement of said front finger grip, said tissue spreading assembly including a plurality of flexible resilient fingers, wherein in the closed position said flexible resilient fingers are withdrawn into said housing segment and in the open position said flexible resilient fingers are extended from said housing segment transversely with respect to said housing segment so that tissues can be spread.

12. The tissue spreading surgical instrument of claim 11 wherein said elongated shaft is rotatable.

13. The tissue spreading surgical instrument of claim 12 further comprising a means for rotating said elongated shaft, said means being located on said outer surface of said proximal end of said rotatable elongated shaft.

14. The spreading surgical instrument of claim 13 wherein said means for rotating said elongated shaft comprises a finger grooved barrel.

15. The tissue spreading surgical instrument of claim 11 wherein said elongated shaft is from 15 to 30 centimeters in length.

16. The tissue spreading surgical instrument of claim 15 wherein the instrument is used in endoscopic surgical procedures.

17. The tissue spreading surgical instrument of claim 16 wherein said plurality of resilient flexible fingers are variable in length, each resilient flexible finger ranging from 2 to 10 centimeters in length.

18. The tissue spreading surgical instrument of claim 16 wherein in the open position, said plurality of resilient flexible fingers are transversely deployed to a width ranging from 5 to 15 centimeters.

* * * * *

UNITED STATES PATENT AND TRADEMARK OFFICE
CERTIFICATE OF CORRECTION

PATENT NO. : 5,690,606

DATED : November 25, 1997

INVENTOR(S) : Gus J. Slotman

It is certified that error appears in the above-indentified patent and that said Letters Patent is hereby corrected as shown below:

Title page, item [54] and Column 1, line 1,
In the title, please delete "Tisssue" and insert therefor
--Tissue--.

Signed and Sealed this

Thirty-first Day of March, 1998

Attest:

BRUCE LEHMAN

Attesting Officer

Commissioner of Patents and Trademarks